United States Patent
Zhu et al.

(10) Patent No.: US 11,661,573 B2
(45) Date of Patent: May 30, 2023

(54) MICROFLUIDIC CHIP FOR CULTURING AND REAL-TIME MONITORING OF MULTICELLULAR TISSUES AND USE METHOD THEREOF

(71) Applicant: SOUTHEAST UNIVERSITY, Nanjing (CN)

(72) Inventors: Zhen Zhu, Nanjing (CN); Qiaodan Li, Nanjing (CN); Dingxin Jin, Nanjing (CN); Feng Yu, Nanjing (CN); Yangye Geng, Nanjing (CN)

(73) Assignee: SOUTHEAST UNIVERSITY, Nanjing (CN)

(*) Notice: Subject to any disclaimer, the term of this patent is extended or adjusted under 35 U.S.C. 154(b) by 486 days.

(21) Appl. No.: 16/960,239

(22) PCT Filed: Apr. 4, 2018

(86) PCT No.: PCT/CN2018/081802
§ 371 (c)(1),
(2) Date: Jul. 6, 2020

(87) PCT Pub. No.: WO2019/183998
PCT Pub. Date: Oct. 3, 2019

(65) Prior Publication Data
US 2021/0071122 A1  Mar. 11, 2021

(30) Foreign Application Priority Data
Mar. 28, 2018 (CN) .......................... 201810262702.5

(51) Int. Cl.
*C12M 3/00* (2006.01)
*B01L 3/00* (2006.01)
(Continued)

(52) U.S. Cl.
CPC .......... *C12M 21/08* (2013.01); *B01L 3/50273* (2013.01); *C12M 23/16* (2013.01);
(Continued)

(58) Field of Classification Search
CPC ...... C12M 21/08; C12M 23/16; C12M 41/46; B01L 3/5027; B01L 2300/0645
See application file for complete search history.

(56) References Cited

U.S. PATENT DOCUMENTS

2003/0020915 A1* 1/2003 Schueller .............. B01L 3/5027 430/1
2018/0100849 A1* 4/2018 Abdolahad ........ G01N 33/5438

* cited by examiner

*Primary Examiner* — Brian J. Sines
(74) *Attorney, Agent, or Firm* — CBM Patent Consulting, LLC

(57) ABSTRACT

A microfluidic chip for culturing and real-time monitoring of multicellular tissues and use method thereof. The chip comprises a glass substrate layer, and a PDMS microchannel layer located on the glass substrate layer, wherein the glass substrate layer comprises a glass substrate, and a plurality of microelectrodes thereon; the PDMS microchannel comprises a plurality of independent microfluidic channels; the microelectrodes on the glass substrate are in one-to-one correspondence with the microfluidic channels in the PDMS microchannel layer; and the microelectrodes are electrically connected to an external circuit. The use method comprises: cell capture, cell or tissue culture, electrical impedance spectroscopy detection, and tissue release.

7 Claims, 6 Drawing Sheets

(51) Int. Cl.
*C12M 3/06* (2006.01)
*C12M 1/34* (2006.01)
(52) U.S. Cl.
CPC ...... *C12M 41/46* (2013.01); *B01L 2300/0645* (2013.01); *B01L 2300/0864* (2013.01); *B01L 2400/0475* (2013.01)

MICROFLUIDIC CHIP FOR CULTURING AND REAL-TIME MONITORING OF MULTICELLULAR TISSUES AND USE METHOD THEREOF

FIELD OF TECHNOLOGY

The present invention relates to the field of microfluidic technologies and tissue culture apparatuses for biological cells, and more particularly to a microfluidic chip for culturing and real-time monitoring of multicellular tissues and use method thereof.

BACKGROUND

Before formal application, a novel drug generally requires two links: animal experiment and human clinical trial. Due to huge differences between animal and human, information provided by animal experiment is unreliable to a certain extent, and the animal experiment relates to ethical problems. In addition, the human clinical trial would bring potential harm to the health of volunteers due to side effects of the drug and other instable factors. On the other hand, there is also huge uncertainty and risk of failure in human clinical trial. Therefore, dynamic in-vitro biological tissue culture and drug experiment are important means to solve problems such as long period of development, high cost and so on.

As an important topic in the field of biological science, in-vitro cell culture is widely used in in-vitro drug test. Conventional two-dimensional cell culture generally uses a petri dish to perform in-vitro culture. However, this method needs a large number of biological samples and experimental consumables; moreover, in-vitro cell culture based on petri dishes cannot simulate the three-dimensional tissue culture and dynamic environment of human body in a more real state. Therefore, it is urgent to find a three-dimensional tissue culture platform between the two-dimensional cell culture and the animal experiment, such that a dynamic growth process of a multicellular tissue can be monitored in real time to obtain dynamic physiological parameters of tissues.

Micro-fluidics-based tissue culture (organ-on-a-chip) is a research hotspot in the field of biological technologies at present. A microfluidic system, which has various alternatives on chip design, tissue culture materials, and methods of fluid control, can be used to mimic and control a tissue microenvironment, perform the three-dimensional tissue culture and in-situ control culture. Therefore, it can be used to study dynamic tissue behavior, physiological and pathological phenomena, novel drug development and screening and the like.

The development of advanced micro-nano fabrication techniques facilitates the application of electric control and detection in the field of microfluidic technology. Dielectrophoresis (DEP) and electrical impedance spectroscopy (EIS) detection are often introduced into a microfluidic chip. Micro-nano-scale metal microelectrodes are integrated in a microfluidic chip by a micro-nano fabrication process. When an electrical signal is applied to the microelectrode, an electroneutral particle in a spatially non-uniform electric field would be polarized and then directionally move under a dielectrophoresis force. When an alternating current voltage with a small amplitude and a swept frequency range is applied to the microelectrode as an excitation signal, a corresponding current signal is acquired as a response signal. Correspondingly, the real-time electrical impedance can be calculated by means of the voltage signal and the current signal, so as to perform electrical impedance detection and analysis on an organism to be detected between the microelectrodes.

At present, the microfluidic chip for tissue culture or drug test has defects in the following aspects which restrict the development and application thereof: there is no effective means in the aspects of precisely operating and controlling a cell and promoting it to grow to be a three-dimensional spherical tissue; the real-time detection at present is generally realized by means of microscopic imaging, and phototoxicity has a certain influence on the physiological state of cells and tissues; high throughput experiments are difficult to perform, and sample data is few, thus lacking statistical significance; it is inconvenient to take out tissue samples to perform subsequent research and experiment. Therefore, the present invention provides special designs for the structure and function of the microfluidic chip, with the purposes of overcoming the above defects, extending the application field thereof, and improving the practical value.

SUMMARY

Object of the present invention: to overcome the defects in the prior art, a microfluidic chip for culturing and real-time monitoring of multicellular tissues and use method thereof are provided.

Technical solution: the present invention provides a microfluidic chip for culturing and real-time monitoring of multicellular tissues; the chip comprises a glass substrate layer, and a PDMS microchannel layer located on the glass substrate layer; the glass substrate layer comprises a glass substrate, and a plurality of microelectrodes thereon; the PDMS microchannel comprises a plurality of independent microfluidic channels; the microelectrodes on the glass substrate are in one-to-one correspondence with the microfluidic channels in the PDMS microchannel layer; the microelectrodes are electrically connected to an external circuit; and different placement modes of the microfluidic chip enable different operation and control functions for cells and tissues.

Preferably, each pair of microelectrodes comprises an A-type microelectrode and a B-type microelectrode; a plurality of tips are disposed on the A-type microelectrode; the tips are used with the B-type microelectrode to for generate a non-uniform electric field around a culture unit; the microelectrode is provided with a contact plate at the edge of the glass substrate; and the contact plate is electrically connected to the external circuit. The contact plate can be reliably and electrically connected to the external circuit via a spring probe.

Preferably, the microfluidic channel comprises a cell suspension inlet, a culture medium inlet, a culture unit, a microchannel outlet, and a microchannel; the cell suspension inlet and the culture medium inlet are disposed at one end of the microchannel, and are in communication with the micro-channel; the micro-channel outlet is disposed at the other end of the micro-channel, and is in communication with the micro-channel; and a plurality of culture units are disposed on the micro-channel, and are in communication with the micro-channel.

Preferably, the microchannel is a Y-shaped structure; the cell suspension inlet and the culture medium inlet are disposed on the two branches of the Y-shaped structure; and the microchannel outlet is located at the other end of the Y-shaped structure. The cell suspension inlet and the culture medium inlet of the PDMS microchannel layer are designed to be a Y-shaped microchannel structure; under the laminar flow regime, cells in the suspension can be precisely controlled to distribute in the microchannel by adjusting the flow rate ratio of the cell suspension to the culture medium, thus cells can be captured at the specified culture unit by the dielectrophoresis force.

Preferably, the culture unit comprises a culture space and a flow guide plate; the culture space interconnects with the microchannel; the flow guide plate is disposed in the microchannel; and the direction of fluid flow in the microchannel is from a wide opening of the flow guide plate to a narrow opening.

Preferably, the culture space is a semi-circular structure.

Wherein the semi-circular culture space provides a growth environment for the cell and the tissue, and is favorable for a suspended cell colony to form a spherical multicellular tissue; the direction of fluid flow in the microchannel is from the wide opening of the flow guide plate to the narrow opening; therefore, when the cell in the suspension is captured or released, the flow guide plate has an effect of flow guide, and can prevent the spherical tissue from leaving the culture unit during culture.

The structure and size parameters of the microchannel and the microelectrodes can be designed according to users' requirements. During the design of a specific microfluidic chip, the length, width, thickness and gap of the microelectrodes can be flexibly designed according to the number and size parameters of the microchannel. The number of the culture units in each microchannel can also be designed according to users' requirements.

Another embodiment of the present invention provides a use method of the microfluidic chip for culturing and real-time monitoring of multicellular tissues, and the method comprises the following steps:

(1) Cell Capture:

Entering a capture mode when the chip is vertically placed and a flow guide plate is above a culture space, first pumping a cell suspension and a culture medium into a microchannel at constant flow rates via a cell suspension inlet and a culture medium inlet respectively, adjusting a flow rate ratio of the cell suspension to the culture solution, and utilizing a microfluidic laminar flow principle to control the distribution of suspended cells in the microchannel;

(2) Tissue Culture:

After a certain number of cells are captured in a culture unit, removing a positive dielectrophoresis force, horizontally placing the chip, entering a tissue culture mode; stopping pumping the cell suspension at the cell suspension inlet, keeping on pumping the culture medium at the culture medium inlet, appropriately reducing the flow rate of the culture medium, and promoting the cells in the culture unit to grow to be a spherical multicellular tissue;

(3) Electrical Impedance Spectroscopy Detection:

Applying an excitation signal to a B-type microelectrode through an electrical impedance spectroscope, acquiring a corresponding response signal from an A-type microelectrode, amplifying and returning it to the electrical impedance spectroscope, and measuring electrical impedance at the culture unit; due to the transparency of glass substrate, the growth state of a multicellular tissue can be monitored in real time by performing microscopic imaging and measuring an impedance change.

(4) Tissue Release: When the Tissue is Cultured to a Certain Stage, Releasing the Tissue Out from the Culture Unit to Perform Subsequent Research Work;

Entering a release mode when the chip is vertically placed and the flow guide plate is under the culture space, sliding the spherical tissue to the microchannel along the flow guide plate, then flowing to the microchannel outlet together with the culture medium pumped from the culture medium inlet, and finally sequentially collecting tissue samples to perform subsequent research work.

Further, in step (1), an alternating current voltage with certain amplitude and frequency is applied across the A-type microelectrode and the B-type microelectrode via an external circuit, such that the cells can be converged in the semi-circular culture space under the positive dielectrophoresis force and the gravity when the cells flow through the culture unit.

The chip is vertically placed during the capture and release processes of the micro particles such as cells and the like. A sufficient positive dielectrophoresis force is generated by applying an alternating current electrical signal with a certain amplitude and frequency to the microelectrodes, so that the cells in the culture unit can directionally move to converge at the bottom of the semi-circular culture space under the positive dielectrophoresis force and the gravity. The chip is horizontally placed during the culture process of the cells or the tissues. The bio-impedance of the cells or tissues is detected by applying an excitation signal to the B-type microelectrode and acquiring a response signal from the A-type microelectrode, so as to monitor the grow state thereof in real time.

Beneficial effects: compared with the prior art, the technical solution of the present invention has the following advantages and beneficial effects:

(1) The microfluidic chip is designed to be vertically placed; with the cooperation of the flow guide plate, the cells directionally move under the dielectrophoresis force and the gravity, so as to achieve cell capture and tissue release;

(2) The microfluidic chip comprising a Y-shaped microfluidic channel structure controls the distribution of the cells in the microchannel by means of laminar flow, thereby facilitating cell capture;

(3) The microfluidic chip, which is integrated with a multifunctional multiplexing microelectrodes, can generate a dielectrophoresis force or perform electrical impedance spectroscopy detection by applying an electrical signal, thus realizing the manipulation and detection of cell or tissues;

(4) The microfluidic chip can be extended with a high integration, wherein more culture units can be integrated in each microfluidic channel, and the number of microfluidic channels and corresponding microelectrodes can also be increased, so as to extend an array-format microfluidic network;

(5) The microfluidic chip is made from a transparent material, which can be used to observe the behavior of cells and tissues in real time through microscope, measure the electrical impedance spectroscopy thereof in real time, acquire a dynamic parameter, and analyze the growth state of cells and tissues;

(6) The microfluidic channels are independent from each other; the culture units in each channel can be treated as a control group to perform experiments; therefore, in-situ control culture of tissues can be performed. Hence, the present invention effectively overcomes the defects in the prior art and lack of application, and offers a high practical value in the field of microfluidics-based tissue culture and real-time monitor.

DESCRIPTION OF THE EMBODIMENTS

Figure 1:
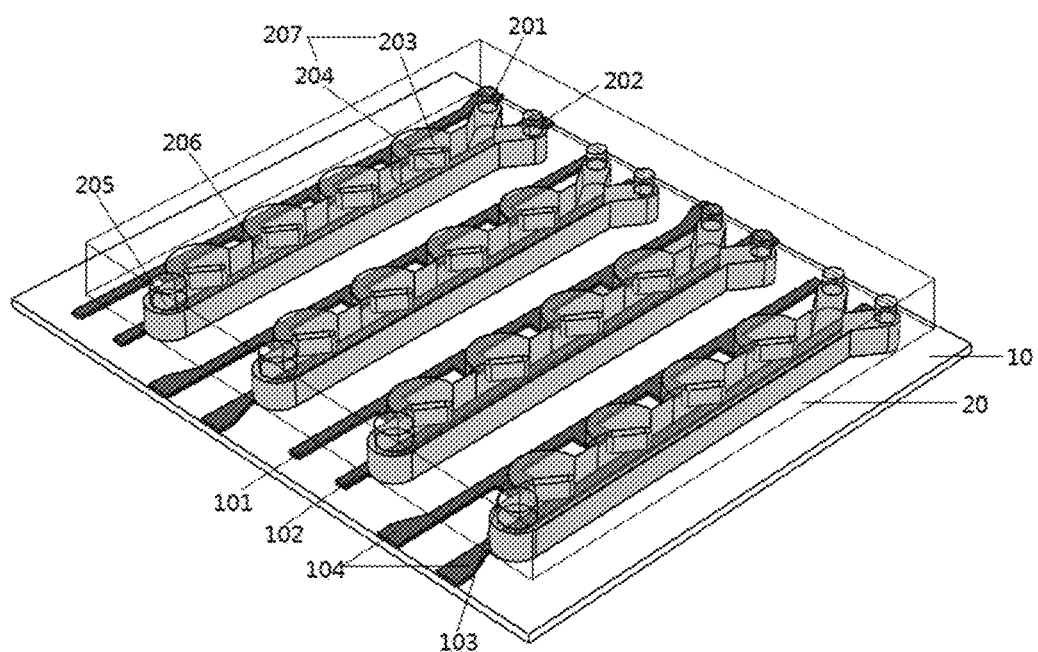
FIG. 1 is a schematic of the three-dimensional structure of the microfluidic chip in the present invention.
Figure 2:
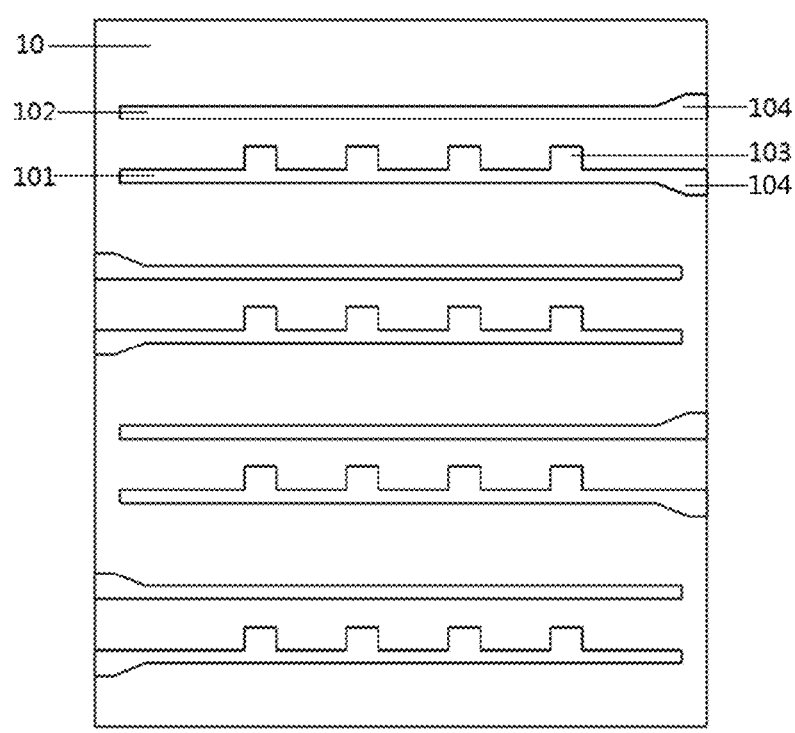
FIG. 2 is a planar structure diagram of a glass substrate.
Figure 3:
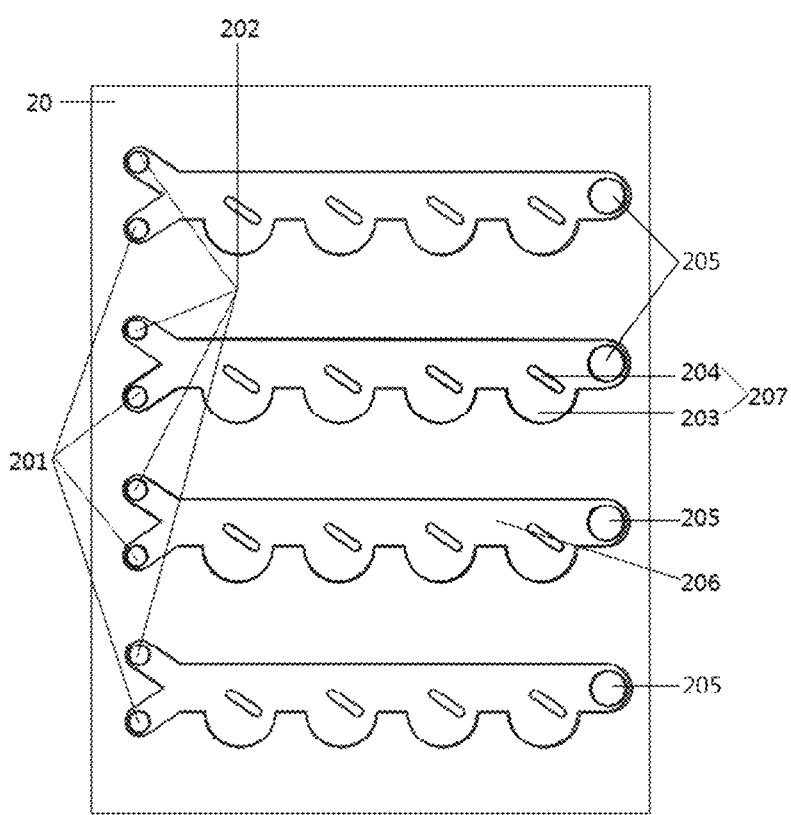
FIG. 3 is a planar structure diagram of a PDMS microchannel layer.
Figure 4:
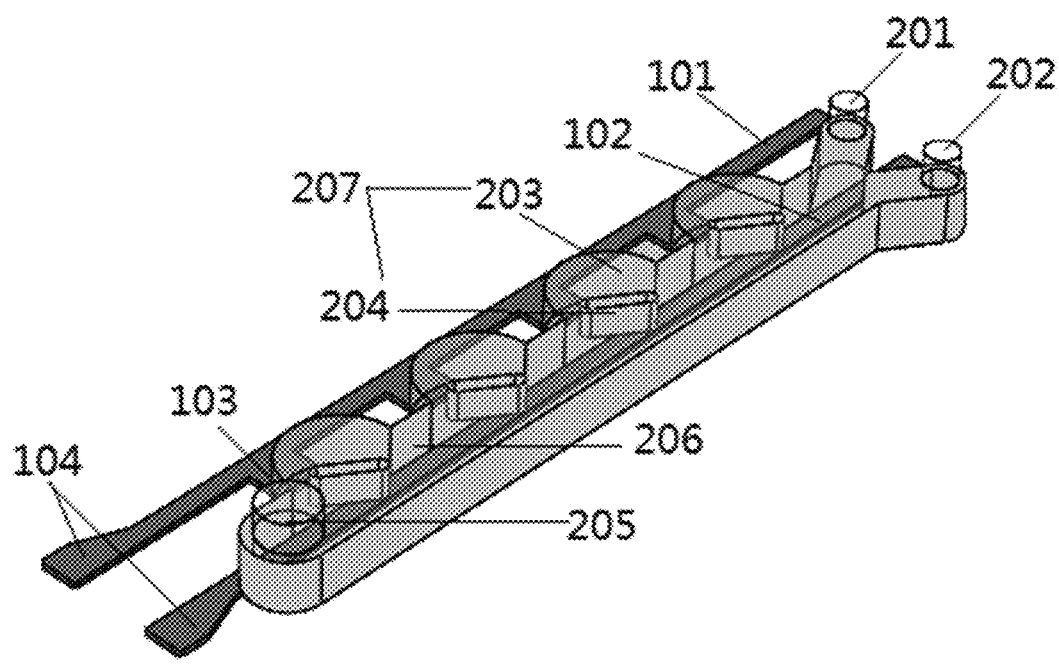
FIG. 4 is a schematic of the three-dimensional structure of a single microfluidic channel.

The technical solution of the present invention will be described in detail hereafter by means of specific embodiments and the drawings. A person skilled in the art can easily understand other advantages and efficacies of the present invention through the disclosures of the specification. The present invention can also be implemented or applied through other different specific embodiments, and the details of the specification can also be modified or changed on the basis of different views and applications without departing from the principle of the present invention.

With reference to FIG. 1-7, it should be noted that, the drawings provided in the embodiments are only intended to illustrate the basic principle, assembly structures, operating process, and efficacies of the present invention in a schematic manner; therefore, the drawings only show the assemblies related to the present invention, but are not drawn according to the number, structures and sizes of the assemblies in practical implementation; when in practical implementation, the shapes, number and proportions of the assemblies can be changed, and the layout of the assemblies may also be more complex.

The present invention provides a microfluidic chip for culturing and real-time monitoring of multicellular tissues; the chip comprises a glass substrate layer 10, and a PDMS microchannel layer 20 located on the glass substrate layer, wherein the glass substrate layer comprises a glass substrate, and a plurality of microelectrode pairs disposed on the glass substrate; the PDMS microchannel comprises a plurality of independent microfluidic channels; the microelectrodes on the glass substrate are in one-to-one correspondence with the microfluidic channels in the PDMS microchannel layer; the microelectrodes are electrically connected to an external circuit; and different placement modes of the microfluidic chip enable different operation and control functions for cells and tissues.

Each pair of microelectrodes comprises an A-type microelectrode 101 and a B-type microelectrode 102 wherein the A-type microelectrode is provided thereon with a plurality of tips 103; the tips are used with the B-type microelectrode to generate a non-uniform electric field around a culture unit, such that the cells in the culture unit can directionally move under the dielectrophoresis force. The A-type microelectrode and the B-type microelectrode are provided with contact plates 104 at the edge of the glass substrate, and the contact plate can be reliably and electrically connected to the external circuit via a spring probe.

Wherein the microfluidic channel comprises a cell suspension inlet 201, a culture medium inlet 202, a culture unit 207, a microchannel outlet 205, and a microchannel 206; the cell suspension inlet and the culture medium inlet are disposed at one end of the microchannel, and interconnect with the microchannel; the microchannel outlet is disposed at the other end of the microchannel, and interconnects with the microchannel; and a plurality of culture units interconnecting fluidic channels are disposed in the microchannel.

The microchannel is a Y-shaped structure; the cell suspension inlet and the culture medium inlet are disposed on the two branches of the Y-shaped structure; and the microchannel outlet is located at the other end of the Y-shaped structure.

The culture unit comprises a culture space 203 and a flow guide plate 204; the culture space is a semi-circular structure, and interconnects with the microchannel; the flow guide plate is disposed in the microchannel; and the direction of fluid flow in the microchannel is from the wide opening of the flow guide plate to the narrow opening, which means the opening angle of the flow guide plate on one side adjacent to the microchannel inlet (the cell suspension inlet 201, and the culture medium inlet 202) is large, and the opening angle on one side adjacent to the microchannel outlet (205) is small.

As shown in FIG. 1-4, a microfluidic chip for culturing and real-time monitoring of multicellular tissues, comprises a glass substrate layer 10 integrated with microelectrodes, and a PDMS microchannel layer 20. The transparent glass substrate is integrated with four pairs of coplanar microelectrodes; each pair of the microelectrodes comprises an A-type microelectrode 101 and a B-type microelectrode 102; the A-type microelectrode comprises a plurality of tips 103; leading-out contact plates of the microelectrodes distributed on the two sides of the glass substrate, are reliably and electrically connected to the external circuit via spring probes; the external circuit applies an alternating current electrical signal to the microelectrodes, so as to achieve dielectrophoresis or bio-impedance detection; the cells or the tissue are/is sequentially manipulated and detected; the PDMS microchannel layer is provided with four independent microfluidic channels, of which each is provided with two inlets and one outlet which are respectively the cell suspension inlet 201, the culture medium inlet 202, and the microchannel outlet 205. The cell suspension inlet and the culture medium inlet are designed to be a Y-shaped microchannel structure; under the laminar flow regime, cells in the suspension can be precisely controlled to distribute in the microchannel by adjusting the flow rate ratio of the cell suspension to the culture medium, thus cells can be captured the cells at the specified culture unit by the dielectrophoresis force. Each microfluidic channel comprises a microchannel 206; four culture units 207 are disposed in the microchannel; the culture unit consists of a semi-circular culture space 203, and a flow guide plate 204. The semi-circular culture space provides a growth environment for the cell and the tissue, and is favorable for a suspended cell colony to form a spherical multicellular tissue; the wide openings of the flow guide plate face the direction of coming fluid flow; therefore, the flow guide plate has an effect flow guide when the cells in the cell suspension are captured by the dielectrophoresis force and when the tissue is released, and can prevent the three-dimensional spherical biological tissue from leaving the culture unit during culture.

The structure and size parameters of the microfluidic channels and the microelectrodes can be designed according to users' requirements. During the design of a specific microfluidic chip, the length, width, thickness and gap of the microelectrodes can be flexibly designed according to the number and size parameters of the microchannels. The number of the culture units in each microchannel can also be designed according to users' requirements.

The chip is vertically placed during the capture and release processes of the micro particles such as cells and the like. A sufficient positive dielectrophoresis force is generated by applying an alternating current electrical signal with a certain amplitude and frequency across the A-type microelectrode and the B-type microelectrode, so that the cells in the culture unit can directionally move to converge at the bottom of the semi-circular culture space under the positive dielectrophoresis force and the gravity. The chip is horizontally placed during the culture process of the cells or the tissues. An alternating current voltage (namely an excitation signal) with a small amplitude and a swept frequency range is applied to the B-type microelectrode via an electrical impedance spectroscope; and a response signal is acquired from the A-type microelectrode via the electrical impedance spectroscope, so as to perform biological electrical impedance spectroscopy detection of cells and tissues, and monitor the growth state thereof in real time.

The microfluidic chip made from transparent materials such as glass, PDMS and the like, enables real-time microscopic observation. In-situ analysis on the dynamic growth and differentiation process of cells or tissues can be performed by combining microscopic images with biological electrical impedance signal, thereby offering application in the fields of cell or tissue biology research, drug screening and the like.

Figure 5:
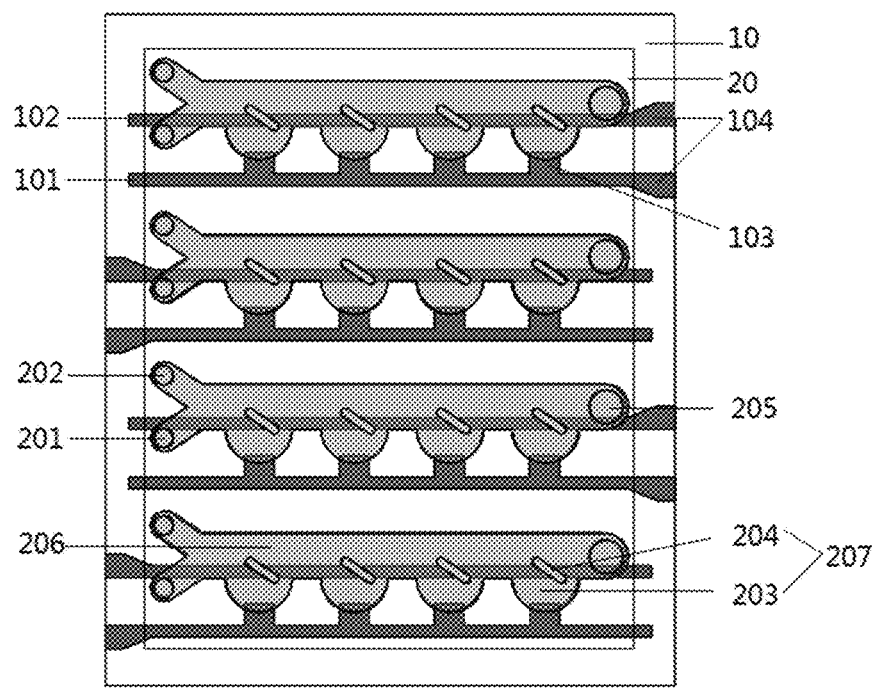
FIG. 5 is a schematic diagram of a vertically placed microfluidic chip during cell capture.
Figure 7:
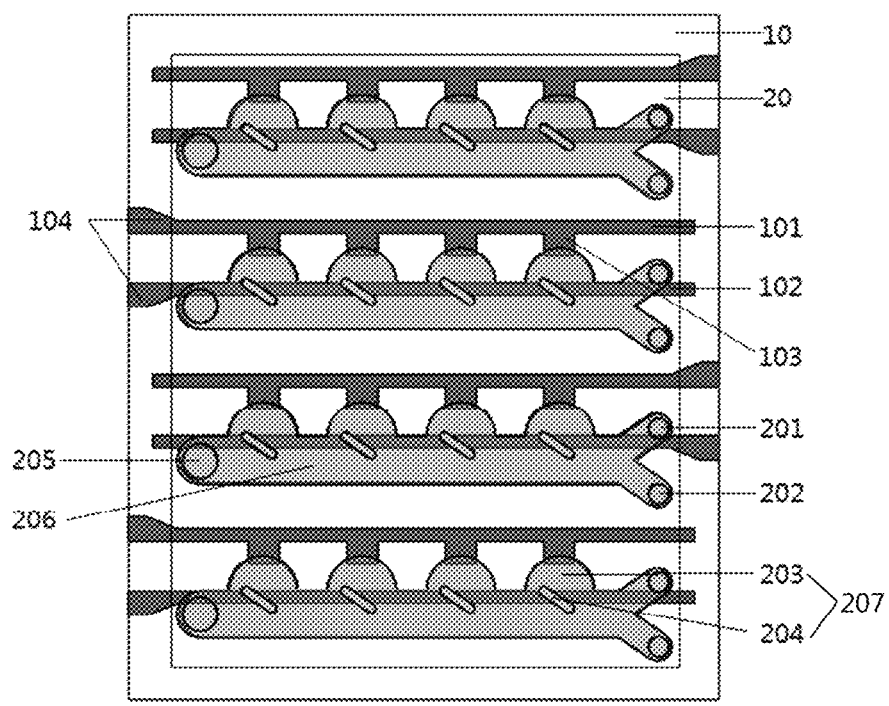
FIG. 7 is a schematic diagram of a vertically placed microfluidic chip during spherical tissue release.

The microfluidic chip can be vertically or horizontally placed when in use, and different placement states can realize different purposes. When the chip is vertically placed (as shown in FIG. 5) and the flow guide plate is above the culture space, the chip enters a capture mode: the cell suspension is perfused into the microchannel; an alternating current electrical signal with a certain amplitude and frequency is applied to the microelectrode, such that the cells in the suspension can move to the culture unit under the positive dielectrophoresis force and the gravity; then the positive dielectrophoresis force is removed, and the cells grows to be a three-dimensional spherical tissue in the semi-circular chamber under the gravity. When the chip is inverted by 180 degrees (as shown in FIG. 7) and the flow guide plate is under the culture space, the chip enters a release mode. The tissue flows into the microchannel along the flow guide plate under the gravity, and then flows out of the microchannel outlet together with the culture medium perfused into the microchannel. During the culture process of cells and tissues, the microelectrodes can perform electrical impedance spectroscopy detection of the physiological processes in the culture unit, such as the formation of the tissue from cells, the growth of the tissue and the like, in order to obtain dynamic biological information thereof and realize real-time, label-free and non-invasive detection.

The chip in the present invention consists of a plurality of microfluidic channels, an array-format culture unit, and a multifunctional microelectrode array corresponding thereto. The microfluidic channels of the chip are independent from each other; each pair of microelectrodes corresponds to the culture unit in one channel. Applying electrical signals with different amplitudes and frequencies to the microelectrodes can realize the functions of generating a dielectrophoresis force, measuring the bio-impedance and the like, such that the cells and the tissues can be manipulated and detected. The innovations of the present invention are the multifunctional multiplexing of the microelectrodes, the vertical placement of the chip, the capture of cells and release of tissues under the gravity and the dielectrophoresis force, as well as the real-time bio-impedance monitoring through the same pair of electrodes during the culture process of cells or tissues. The chip in the present invention is made from a transparent substrate, thus in-situ observation and analysis of the dynamic growth and physiological behavior of cells, tissues and the like can be performed by using microscopic imaging as a complementary means of electrical impedance spectroscopy. The present invention can be used in the fields of cell or tissue biology research, drug screening and the like.

When in specific use in the embodiment, the use method of the microfluidic chip for tissue culture and drug experiment comprises at least the following steps:

The chip integrates the functions of cell capture, culture, tissue release, and detection. The steps will be described according to different functions.

(1) Cell capture:

Entering the capture mode when the chip is vertically placed and the flow guide plate is above the culture space, as shown in FIG. 5; first pumping the cell suspension and the culture medium into the microchannel 206 at constant flow rates via the cell suspension inlet 201 and the culture medium inlet 202 respectively; adjusting the flow rate ratio of the cell suspension to the culture solution to control the distribution of suspended cells in the microchannel 206.

Further, an alternating current voltage with certain amplitude and frequency is applied to the microelectrodes 101 and 102 via the external circuit, such that the cells can be converged in the semi-circular culture space 203 under the positive dielectrophoresis force and the gravity when the cells flow through the culture unit. In such process, the flow guide plate has an effect of flow guide for the directional movement of the cells.

Figure 6:
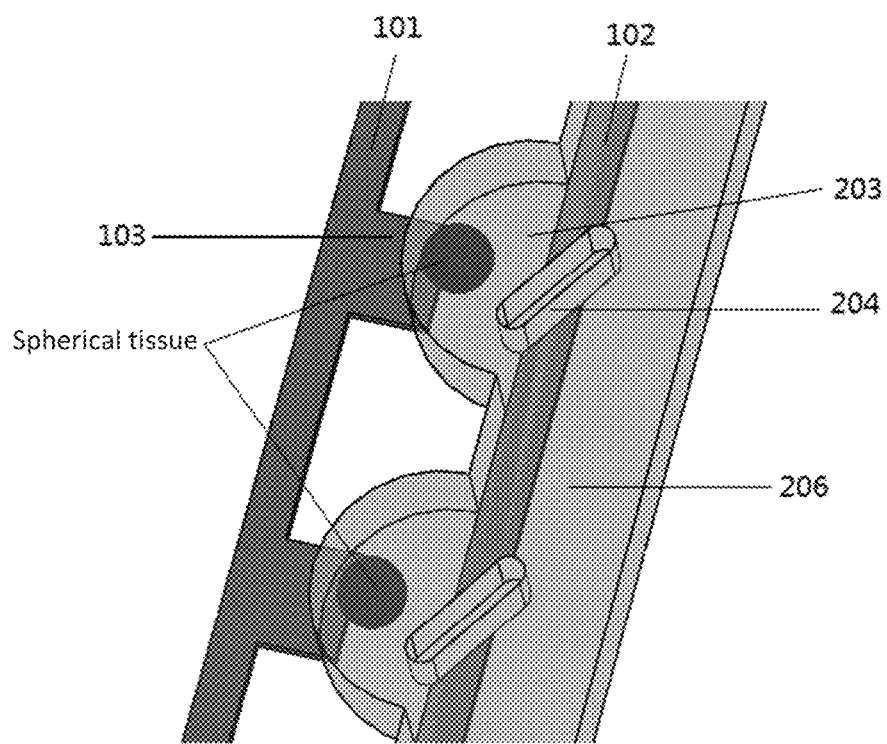
FIG. 6 is a schematic diagram of a spherical tissue formed by the growth of a cell colony in a culture unit.

(2) Tissue culture:

After a certain number of cells are captured in a culture unit, removing a positive dielectrophoresis force, horizontally placing the chip, entering a tissue culture mode; stopping pumping the cell suspension at the cell suspension inlet 201, keeping on pumping the culture medium at the culture medium inlet 202, appropriately reducing the flow rate of the culture medium, and promoting the cells in the culture unit to grow to be a spherical multicellular tissue, as shown in FIG. 6.

(3) Electrical impedance spectroscopy detection:

Applying an excitation signal to a B-type microelectrode through an electrical impedance spectroscope, acquiring a corresponding response signal from an A-type microelectrode, amplifying and returning it to the electrical impedance spectroscope, and measuring electrical impedance at the culture unit. Due to the transparency of glass substrate, the growth state of a multicellular tissue can be monitored in real time by performing microscopic imaging and measuring an impedance change.

(4) Tissue release: when the tissue is cultured to a certain stage, releasing the tissue out from the culture unit to perform subsequent research work;

Entering the release mode when the chip is vertically placed and the flow guide plate 204 is under the culture space 203, as shown in FIG. 7; Sliding the spherical tissue to the microchannel 206 along the flow guide plate, then flowing to a microchannel outlet 205 together with the culture medium pumped from the culture medium inlet 202, and finally sequentially collecting tissue samples.

The microfluidic chip is fabricated using a micro-nano fabrication process which comprises the following steps:

(1) Using a lift-off process to pattern a transparent ITO, Au or Pt microelectrode array on a glass wafer, and then dicing the wafer for bonding;

(2) Utilizing a ultraviolet lithography process of SU-8 photoresist to fabricate a mold for the PDMS microchannel on a silicon wafer;

(3) Placing thoroughly-mixed liquid polydimethyl siloxane (PDMS) (base material:solidifying agent=10:1) on the mold, baking it for two hours at 80° C., solidifying, stripping, cutting, punching, to prepare a PDMS microchannel layer for bonding;

(4) Treating the glass substrate patterned with microelectrodes and the PDMS micro-channel layer with oxygen plasma, then aligning the PDMS microchannel layer with the glass substrate under a stereo-microscope, pressing to realize permanent bonding, and finally forming the microfluidic chip.

In the present application, the electrical connection mode can adopt an electrical connection mode in the prior art, or the following setup steps of experiment platform.

The setup of an experiment platform comprises the following steps:

(1) Placing the microfluidic chip on the custom-made aluminum holder;

(2) Placing a transparent PMMA cover comprising a plurality of thread holes on the microfluidic chip, and fixing the PMMA cover and the aluminum holder via plastic screws, wherein the microfluidic chip is fixed between them;

(3) Placing a printed circuit board comprising a control circuit and spring probes on the PMMA cover; using plastic screws to fix the printed circuit board. The spring probes which penetrate through the holes on the PMMA cover are reliably and electrically connected to the contact plate led out from an electrode in the microfluidic chip. The signal source and the electrical impedance spectroscope can also be connected to the microelectrodes of the microfluidic chip via the printed circuit board.

In the present invention, the microfluidic chip integrates the functions of cell or tissue manipulation, culture, real-time detection and the like. Since the microfluidic channels of the chip are independent from each other, each microfluidic channel and the culture units thereof can be treated as a control group; therefore, the chip can be used to perform multiple groups of control experiments to test the influence of different culture medium or drugs on the tissues. In the present invention, the microelectrode is multiplexed and multifunctional; during cell capture, the cells are captured under the dielectrophoresis force and the gravity; during tissue release, the tissue is released under the gravity; during cell and tissue culture, the electrical impedance spectroscopy detection is performed to realize real-time monitoring, so as to obtain dynamic information (such as size, viability, apoptosis and the like). In addition, the microfluidic chip can be scaled up by integrating more microchannels and increasing culture units in each microchannel, thereby facilitating high-throughput drug experiments based on three-dimensional spherical tissues. Therefore, the chip can be widely used in tissue culture and drug screening experiments.

The above embodiments are intended to illustratively describe the basic principle, assembly structures, operating process and efficacies of the present invention only, but not to limit the application of the present invention. A person skilled in the art can modify or change the above embodiments without departing from the principle of the present invention. Therefore, any modifications or variations made by an ordinary person skilled in the art without departing from the principle and technical concept of the present invention should be all concluded in the protection scope of the present invention and covered by the claims of the present invention.

What is claimed is:

1. A microfluidic chip for culturing and real-time monitoring of multicellular tissues, the chip comprising a glass substrate layer (10), and a PDMS microchannel layer (20) located on the glass substrate layer; the glass substrate layer comprises a glass substrate and a plurality of microelectrodes thereon; the PDMS microchannel layer comprises a plurality of independent microfluidic channels; the microelectrodes on the glass substrate are in one-to-one correspondence with the microfluidic channels in the PDMS microchannel layer; the microelectrodes are electrically connected to an external circuit; and different placement modes of the microfluidic chip enable different operation and control functions for cells and tissues;

wherein each pair of microelectrodes comprises an A-type microelectrode (101) and a B-type microelectrode (102); a plurality of tips (103) are disposed on the A-type microelectrode; the tips are used with the B-type microelectrode to generate a non-uniform electric field around a culture unit; the microelectrode is provided with a contact plate (104) at the edge of the glass substrate; and the contact plate is electrically connected to the external circuit.

2. The microfluidic chip for culturing and real-time monitoring of multicellular tissues according to claim 1, wherein the microfluidic channel comprises a cell suspension inlet (201), a culture medium inlet (202), a culture unit (207), a microchannel outlet (205), and a microchannel (206); the cell suspension inlet and the culture medium inlet are disposed at one end of the microchannel, and interconnect with the microchannel; the microchannel outlet is disposed at the other end of the microchannel, and interconnects with the microchannel; and a plurality of culture units interconnecting fluidic channels are disposed in the microchannel.

3. The microfluidic chip for culturing and real-time monitoring of multicellular tissues according to claim 2, wherein the microchannel is a Y-shaped structure; the cell suspension inlet and the culture medium inlet are disposed on the two branches of the Y-shaped structure; and the microchannel outlet is located at the other end of the Y-shaped structure.

4. The microfluidic chip for culturing and real-time monitoring of multicellular tissues according to claim 2, wherein the culture unit comprises a culture space (203) and a flow guide plate (204); the culture space interconnects with the microchannel; the flow guide plate is disposed in the microchannel; and the direction of fluid flow in the microchannel is from the wide opening of the flow guide plate to the narrow opening.

5. The microfluidic chip for culturing and real-time monitoring of multicellular tissues according to claim 4, wherein the culture space is a semi-circular structure.

6. The microfluidic chip for culturing and real-time monitoring of multicellular tissues according to claim 2, wherein the microfluidic chip is used by the following steps:

i) entering a capture mode when the chip is vertically placed and the flow guide plate is above a culture space, first pumping a cell suspension and a culture medium into a microchannel at constant flow rates via a cell suspension inlet and a culture medium inlet respectively, adjusting a flow rate ratio of the cell suspension to the culture medium, and utilizing a microfluidic laminar flow principle to control the distribution of suspended cells in the microchannel;

ii) removing a positive dielectrophoresis force, horizontally placing the chip, entering a tissue culture mode after a certain number of cells are captured in the culture unit; stopping pumping the cell suspension at the cell suspension inlet, keeping on pumping the culture medium at the culture medium inlet, appropriately reducing the flow rate of the culture medium, and promoting the cells in the culture unit to grow to be a spherical multicellular tissue;

iii) applying an excitation signal to the B-type microelectrode through an electrical impedance spectroscope, acquiring a corresponding response signal from the A-type microelectrode, amplifying and returning it to the electrical impedance spectroscope, and measuring electrical impedance at the culture unit; due to the transparency of the glass substrate, the growth state of a multicellular tissue can be monitored in real time by performing microscopic imaging and measuring an impedance change; and iv) entering a release mode when the chip is vertically placed and the flow guide plate is under the culture space, sliding the spherical tissue to the microchannel along the flow guide plate, then flowing to the microchannel outlet together with the culture medium pumped from the culture medium inlet, and finally sequentially collecting tissue samples to perform subsequent research work.

7. The microfluidic chip for culturing and real-time monitoring of multicellular tissues according to claim 6, wherein in the step i), an alternating current voltage with certain amplitude and frequency is applied across the A-type microelectrode and the B-type microelectrode via an external circuit, such that the cells can be converged in the semicircular culture space under the positive dielectrophoresis force and the gravity when the cells flow through the culture unit.

* * * * *